(12) United States Patent
Lee et al.

(10) Patent No.: US 9,717,708 B1
(45) Date of Patent: Aug. 1, 2017

(54) PROCESS FOR PREPARING ERTAPENEM-CONTAINING LYOPHILIZED FORMULATION

(71) Applicant: DAEWOONG PHARMACEUTICAL CO., LTD., Seongnam-si, Gyeonggi-do (KR)

(72) Inventors: Bong-Yong Lee, Yongin-si (KR); Hee-Kyoon Yoon, Cheongju-si (KR); Wol-Young Kim, Seongnam-si (KR); Jeong-Taek Shin, Yongin-si (KR)

(73) Assignee: DAEWOONG PHARMACEUTICAL CO., LTD., Seongnam-si, Gyeonggi-do (KR)

( * ) Notice: Subject to any disclaimer, the term of this patent is extended or adjusted under 35 U.S.C. 154(b) by 0 days.

(21) Appl. No.: 15/503,940

(22) PCT Filed: Jul. 28, 2015

(86) PCT No.: PCT/KR2015/007828
§ 371 (c)(1),
(2) Date: Feb. 14, 2017

(87) PCT Pub. No.: WO2016/028002
PCT Pub. Date: Feb. 25, 2016

(30) Foreign Application Priority Data

Aug. 20, 2014 (KR) .................. 10-2014-0108079

(51) Int. Cl.
*A61K 31/407* (2006.01)
*A61K 9/16* (2006.01)
*A61K 9/19* (2006.01)

(52) U.S. Cl.
CPC .......... *A61K 31/407* (2013.01); *A61K 9/1652* (2013.01); *A61K 9/1682* (2013.01); *A61K 9/19* (2013.01)

(58) Field of Classification Search
None
See application file for complete search history.

(56) References Cited

U.S. PATENT DOCUMENTS

| | | |
|---|---|---|
| 6,486,150 B2 | 11/2002 | Hunke et al. |
| 6,548,492 B1 | 4/2003 | Al-Dehneh et al. |
| 8,183,233 B2 | 5/2012 | Kipp et al. |
| 2002/0002160 A1 | 1/2002 | Hunke et al. |
| 2009/0286764 A1 | 11/2009 | Kipp et al. |
| 2012/0207762 A1 | 8/2012 | Kipp et al. |

FOREIGN PATENT DOCUMENTS

KR    10-0756595 B1    9/2007

*Primary Examiner* — Michael Barker
(74) *Attorney, Agent, or Firm* — Vorys, Sater, Seymour & Pease LLP; Mih Suhn Koh

(57) ABSTRACT

The present invention provides a process for preparing an ertapenem-containing lyophilized formulation, comprising the use of hydroxypropyl β-cyclodextrin as both a cryoprotective agent and a stabilizing agent.

5 Claims, 3 Drawing Sheets

PROCESS FOR PREPARING ERTAPENEM-CONTAINING LYOPHILIZED FORMULATION

TECHNICAL FIELD

The present invention relates to a process for preparing an ertapenem-containing lyophilized formulation. More specifically, the present invention relates to an improved process for preparing an ertapenem-containing lyophilized formulation, comprising the use of hydroxypropyl β-cyclodextrin as both a cryoprotective agent and a stabilizing agent.

BACKGROUND ART

Ertapenem is one of the carbapenem antibiotics and its chemical name is (4R,5S,6S)-3-[(3S,5S)-5-[(3-carboxyphenyl)carbamoyl]pyrrolidin-3-yl]sulfanyl-6-(1-hydroxyethyl)-4-methyl-7-oxo-1-azabicyclo[3.2.0]hept-2-ene-2-carboxylic acid. The chemical structure of ertapenem is as follow:

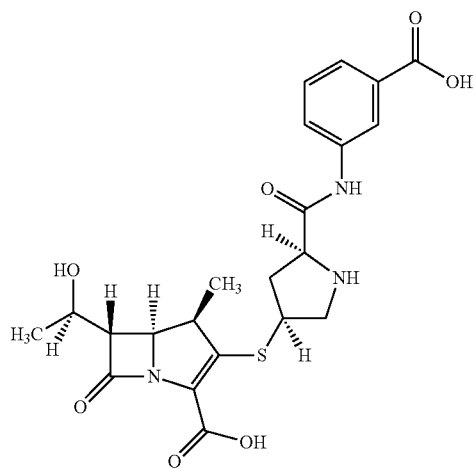 [SMILES: C[C@@H](O)[C@H]1C(=O)N2C(C(=O)O)=C(S[C@@H]3CN[C@H](C(=O)Nc4cccc(C(=O)O)c4)C3)[C@H](C)[C@H]12]

Ertapenem is a weakly crystalline solid, hygroscopic at ambient conditions, and is unstable at room and refrigerated temperatures. Ertapenem is prepared in large batches as a salt form, i.e., monosodium salt form. Because ertapenem is unstable at a temperature more than about −20° C., the bulk compound should be stored at low temperature (about −20° C.) to prevent degradation into dimer and open ring by-products. Although the unstable carbapenem after bulk manufacturing can be stored for long periods of time at a low temperature, the bulk compound should be converted into a stable formulation prior to use as once-a-day antimicrobial agent for intravenous (IV) and intramuscular (IM) administration. Currently, ertapenem is formulated into a lyophilized formulation, which is used as an injection form in clinical practices.

Korean Patent No. 10-0756595 has disclosed a process for preparing an ertapenem-containing lyophilized formulation including the use of carbon dioxide sources such as $NaHCO_3$ as an additive. However, when a lyophilized formulation is prepared according to Korean Patent No. 10-0756595, ertapenem-derived degradation products are increased in the step for lyophilizing the solution containing the carbon dioxide sources such as $NaHCO_3$ and the bulk compound, which results in lowering the amount thereof. And also, even when the obtained lyophilized formulation is stored at low temperature (about −20° C.), the stability thereof is also decreased due to degradation product formation.

Therefore, there is a need to develop a process for preparing a lyophilized formulation which can solve both the decreased purity during the lyophilizing step and the decreased stability of the obtained lyophilized formulation.

DISCLOSURE

Technical Problem

The present inventors carried out various researches in order to develop an improved process for preparing an ertapenem-containing lyophilized formulation. Surprisingly, the present inventors have found that hydroxypropyl β-cyclodextrin can function as a stabilizing agent in an ertapenem-containing lyophilized formulation as well as a cryoprotective agent (i.e., cryoprotectant) during the lyophilizing step.

Therefore, the present invention provides a process for preparing an ertapenem-containing lyophilized formulation, comprising the use of hydroxypropyl β-cyclodextrin as both a cryoprotective agent and a stabilizing agent.

Technical Solution

In accordance with an aspect of the present invention, there is provided a process for preparing an ertapenem-containing lyophilized formulation, comprising (a) dissolving ertapenem or its pharmaceutically acceptable salt in a solution of hydroxypropyl β-cyclodextrin, while maintaining the pH of the solution in the range of 6.5 to 8.0; and (b) lyophilizing the solution obtained in the step (a).

In the process according to the present invention, the hydroxypropyl β-cyclodextrin may have a molar substitution ranging from 0.6 to 0.9. And also, the hydroxypropyl β-cyclodextrin may be used in a ratio of 0.5 to 2.0 equivalents per 1 equivalent of ertapenem or its pharmaceutically acceptable salt.

In an embodiment, the pharmaceutically acceptable salt of ertapenem is ertapenem monosodium salt. In another embodiment, the pH may be adjusted with a base selected from the group consisting of sodium hydroxide, sodium bicarbonate, sodium carbonate, sodium methoxide, sodium ethoxide, and sodium t-butoxide.

Advantageous Effects

It has been found by the present invention that hydroxypropyl β-cyclodextrin can function as a stabilizing agent in an ertapenem-containing lyophilized formulation as well as a cryoprotective agent (i.e., cryoprotectant) during the lyophilizing step. Therefore, the process of the present invention can provide an ertapenem-containing lyophilized formulation which is able to maintain high purity for extended period.

BEST MODE

Figure 1:
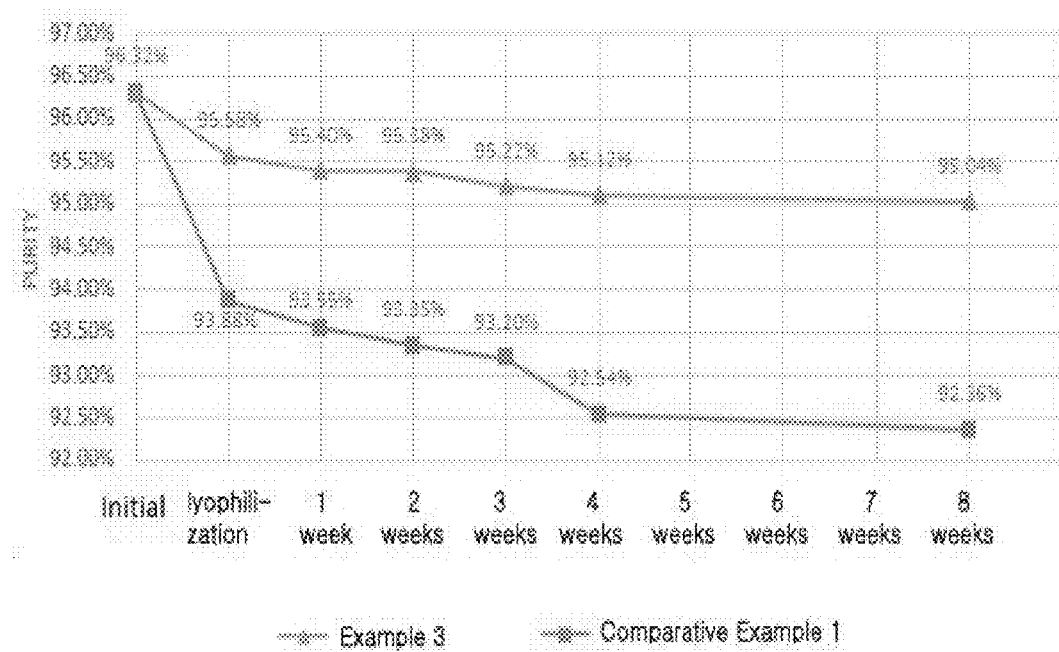
FIG. 1 shows the results obtained by measuring the purity changes of ertapenem in both the lyophilized formulation using NaHCO$_3$ as an additive and the lyophilized formulation prepared according to the present invention, at the preparations thereof; and then during the storages thereof at low temperature (−20° C.).

The present invention provides a process for preparing an ertapenem-containing lyophilized formulation, comprising (a) dissolving ertapenem or its pharmaceutically acceptable salt in a solution of hydroxypropyl β-cyclodextrin, while maintaining the pH of the solution in the range of 6.5 to 8.0; and (b) lyophilizing the solution obtained in the step (a).

It has been found by the present invention that hydroxypropyl β-cyclodextrin can function as a stabilizing agent in an ertapenem-containing lyophilized formulation as well as a cryoprotective agent (i.e., cryoprotectant) during the lyophilizing step. It has been also found by the present invention that, unlike hydroxypropyl β-cyclodextrin, solutions containing other polyhydric alcohols cannot provide stabilizing effects, in comparison with the solution containing the carbon dioxide sources. Especially, it has been found by the present invention that, in lyophilized formulations containing other carbapenem antibiotics (e.g., doripenem and meropenem), hydroxypropyl β-cyclodextrin cannot function as a cryoprotective agent nor as a stabilizing agent, which is different from the lyophilized formulation containing ertapenem. Therefore, only a specific polyhydric alcohol, i.e., hydroxypropyl β-cyclodextrin, functions both as a cryoprotective agent and as a stabilizing agent in a lyophilized formulation containing the specific carbapenem antibiotic, i.e., ertapenem.

In the process of the present invention, ertapenem or its pharmaceutically acceptable salt may be used in a therapeutically effective amount, which can be determined from prior arts. For example, ertapenem or its pharmaceutically acceptable salt may be used in an amount ranging from about 0.1 to 1 g per unit formulation (i.e., per unit lyophilized formulation). In an embodiment, the pharmaceutically acceptable salt of ertapenem is ertapenem monosodium salt.

The hydroxypropyl β-cyclodextrin may have a molar substitution ranging from 0.6 to 0.9. Preferably, hydroxypropyl β-cyclodextrin may have a molar substitution of 0.65 or 0.85. And also, the hydroxypropyl β-cyclodextrin may be used in a ratio of 0.5 to 2.0 equivalents per 1 equivalent of ertapenem or its pharmaceutically acceptable salt.

The pH may be adjusted with a conventional base used in the field of pharmaceutics, for example with a base selected from the group consisting of sodium hydroxide, sodium bicarbonate, sodium carbonate, sodium methoxide, sodium ethoxide, and sodium t-butoxide.

The dissolving of Step (a) is carried out by dissolving ertapenem or its pharmaceutically acceptable salt in a solution of hydroxypropyl β-cyclodextrin. Ertapenem or its pharmaceutically acceptable salt may be added to the solution at a time. Preferably, ertapenem or its pharmaceutically acceptable salt is added to the solution in a plurality of portions over about 60 minutes. And also, the dissolving may be carried out preferably at low temperature (for example, 0~5° C.), so as to minimize the formation of ertapenem-derived degradation products.

The lyophilizing of Step (b) may be carried out with a conventional lyophilizer according to a conventional method in the field of pharmaceutics. Before performing the lyophilizing step, the solution obtained in Step (a) may be filled in an appropriate vessel (e.g., vial, etc.). The lyophilizing may be performed until the resulting lyophilized formulation has a moisture content preferably not more than about 13%, more preferably ranging from 2 to 10%.

The present invention will be described in further detail with reference to the following examples. These examples are for illustrative purposes only and are not intended to limit the scope of the present invention.

Example 1: Evaluation on Stabilizing Effects of Hydroxypropyl β-Cyclodextrin

Hydroxypropyl β-cyclodextrin (HP-β-CD) [molar substitution (MS): 0.65 or 0.85] was dissolved in distilled water (16 mL), according to the amounts shown in Table 1. After cooling each solution to 0~5° C., 10 portions of ertapenem monosodium salt (1 g in total, each portion having the same amount) were sequentially added to each solution for 60 minutes, while maintaining pH 7.8 with a 2N NaOH solution. While the resulting each solution was stored at 0~5° C. for 4 hours, each purity of ertapenem in the solution was measured. For comparison, the solution was prepared according to the same method, except for using NaHCO$_3$ (0.175 g, 1.0 eq.) instead of hydroxypropyl β-cyclodextrin; and then while the solution was stored at 0~5° C. for 4 hours, each purity of ertapenem in the solution was measured. The results are shown in the following Table 1.

TABLE 1

| | Additive | Amount of Additive eq. | Amount of Additive g | MS | Purity 0 h | Purity 2 h | Purity 4 h | Δ Purity |
|---|---|---|---|---|---|---|---|---|
| Comparative Example | NaHCO$_3$ | 1.00 | 0.175 | — | 96.39% | 96.04% | 95.83% | −0.56% |
| 1-1 | HP-β-CD | 0.00 | 0.00 | 0.65 | 96.04% | 95.33% | 94.60% | −1.44% |
| 1-2 | | 0.10 | 0.28 | 0.65 | 95.99% | 95.52% | 95.04% | −0.95% |
| 1-3 | | 0.17 | 0.47 | 0.65 | 96.31% | 95.82% | 95.59% | −0.72% |
| 1-4 | | 0.30 | 0.83 | 0.65 | 96.01% | 95.53% | 95.45% | −0.56% |
| 1-5 | | 0.50 | 1.38 | 0.65 | 96.09% | 95.94% | 95.70% | −0.39% |
| 1-6 | | | | 0.85 | 96.54% | 96.29% | 96.00% | −0.54% |
| 1-7 | | 0.70 | 1.94 | 0.65 | 96.09% | 95.91% | 95.80% | −0.29% |
| 1-8 | | | | 0.85 | 96.27% | 95.95% | 95.78% | −0.49% |
| 1-9 | | 1.00 | 2.76 | 0.65 | 96.30% | 96.01% | 96.09% | −0.21% |
| 1-10 | | | | 0.85 | 96.25% | 95.96% | 95.80% | −0.45% |
| 1-11 | | 1.50 | 4.15 | 0.65 | 96.01% | 95.85% | 95.74% | −0.27% |
| 1-12 | | 2.00 | 5.53 | 0.65 | 96.23% | 95.97% | 95.92% | −0.31% |

As shown in Table 1, when hydroxypropyl β-cyclodextrin having molar substitution ranging from 0.6 to 0.9, preferably molar substitution of 0.65 or 0.85, was used in a ratio of 0.5 to 2.0 equivalents per 1 equivalent of ertapenem or its salt, the resulting solutions showed the same or more stabilities, in comparison with the solution containing a carbon dioxide source. Especially, when hydroxypropyl β-cyclodextrin having molar substitution of 0.65 was used in the ratio of 1 equivalent per 1 equivalent of ertapenem or its salt, the purity change of ertapenem in the resulting solution was reduced by more than 2 times, in comparison with that in the solution containing a carbon dioxide source.

Example 2: Evaluation on Stabilizing Effects of Polyhydric Alcohols

Stabilizing effects in ertapenem-containing solutions were evaluated, using polyhydric alcohols other than hydroxypropyl β-cyclodextrin. Solutions were prepared according to the same method as in Example 1, using various polyhydric alcohols shown in Table 2. While the resulting solutions were stored at 0~5° C. for 4 hours, the purities of ertapenem in the solutions were measured. The results are shown in the following Table 2.

TABLE 2

| Additive | Amount of Additive (g) | Purity 0 h | 1 h | 2 h | 3 h | 4 h | Δ Purity |
|---|---|---|---|---|---|---|---|
| NaHCO$_3$ | 0.175 | 96.39% | 96.31% | 96.04% | 95.74% | 95.83% | −0.56% |
| Poloxamer 188 | 0.5 | 96.63% | 96.27% | 95.77% | 95.27% | 95.18% | −1.45% |
| | 1.0 | 96.35% | 96.18% | 95.91% | 95.61% | 95.38% | −0.97% |
| | 1.5 | 96.44% | 96.25% | 96.00% | 95.65% | 95.49% | −0.95% |
| Polyethylene glycol 300 | 0.5 | 96.50% | 96.17% | 96.15% | 95.64% | 95.59% | −0.91% |
| | 1.0 | 96.48% | 96.17% | 96.09% | 95.58% | 95.56% | −0.92% |
| Polyethylene glycol 600 | 0.5 | 96.46% | 96.13% | 95.76% | 95.51% | 95.27% | −1.19% |
| | 1.0 | 96.44% | 96.16% | 95.79% | 95.55% | 95.31% | −1.13% |
| Polyoxyl 35 Castor oil | 0.5 | 96.60% | 96.25% | 95.86% | 95.61% | 95.31% | −1.29% |
| Methyl cellulose | 0.5 | 96.50% | 95.75% | 95.04% | 94.87% | 94.85% | −1.65% |

From the results of Table 2, it can be seen that, unlike hydroxypropyl β-cyclodextrin, the solutions containing other polyhydric alcohols did not provide stabilizing effects, in comparison with the solution containing the carbon dioxide source.

Example 3: Preparation of Lyophilized Formulation and Evaluation Thereof

Hydroxypropyl β-cyclodextrin (HP-β-CD) [MS=0.65, 2.76 g (1.0 eq.)] was dissolved in distilled water (16 mL). After cooling the solution to 0~5° C., 10 portions of ertapenem monosodium salt (1 g in total, each portion having the same amount) were sequentially added to the solution for 60 minutes, while maintaining pH 7.8 with a 2N NaOH solution. The resulting solution was sterile-filtered at 0~5° C., filled in a vial, and then lyophilized as follows: The filled vial was located on the shelf of a lyophilizer precooled to −40° C. and then cooled for 3 hours. Vacuum (80 mTorr) was applied to the shelf, which was then heated to −20° C. at the rate of 0.5° C./min. The shelf was maintained under the conditions of −20° C. and 80 mTorr for 48 hours. The shelf was heated to 10° C. at the rate of 0.1° C./min and then to 40° C. at the rate of 0.5° C./min. The shelf was maintained under the conditions of 40° C. and 80 mTorr for 3 hours. The shelf was additionally heated to 60° C. at the rate of 0.5° C./min, maintained under the conditions of 60° C. and 80 mTorr for 3 hours, and then cooled to 25° C. for completion of the lyophilization. For comparison, the solution was prepared according to the same method, except for using NaHCO$_3$ (0.175 g, 1.0 eq.) instead of hydroxypropyl β-cyclodextrin; and then the resulting solution was sterile-filtered, filled in a vial, and then lyophilized, according to the same methods as described in the above. All the obtained lyophilized formulations have moisture contents of about 2~10%.

The purities of ertapenem before the lyophilization, the purities of ertapenem right after the lyophilization, and the purities of ertapenem after the lyophilized formulations were stored at low temperature (−20° C.), at room temperature, and under the accelerated (40° C., RH75%) condition for 8 weeks were respectively measured with a HPLC. The results are shown in the following Table 3 and FIGS. 1 to 3.

drate and meropenem trihydrate instead of ertapenem monosodium salt. The purities before the lyophilization, the purities right after the lyophilization, and the purities of the lyophilized formulations which were respectively stored at low temperature (−20° C.), at room temperature, and under the accelerated (40° C., RH75%) condition for 4 weeks were respectively measured with a HPLC. The results are shown in the following Table 4 (doripenem) and Table 5 (meropenem).

TABLE 3

| | Additive | Storage condition | Before the lyophilization | Right after the lyophilization | Purity | | | | |
|---|---|---|---|---|---|---|---|---|---|
| | | | | | 1 week | 2 weeks | 3 weeks | 4 weeks | 8 weeks |
| Comparative Example 1 | NaHCO3 | −20° C. | 96.32% | 93.88% | 93.55% | 93.35% | 93.20% | 92.54% | 92.36% |
| | | Room temperature | | | 92.96% | 92.44% | 91.62% | 91.49% | 88.14% |
| | | 40° C., 75% | | | 90.42% | 85.47% | 85.45% | 85.19% | 71.73% |
| Example 3 | HP-β-CD | −20° C. | | 95.58% | 95.40% | 95.38% | 95.22% | 95.12% | 95.04% |
| | | Room temperature | | | 95.25% | 95.21% | 95.02% | 94.77% | 94.23% |
| | | 40° C., 75% | | | 94.01% | 92.94% | 92.59% | 91.43% | 87.48% |

Figure 2:
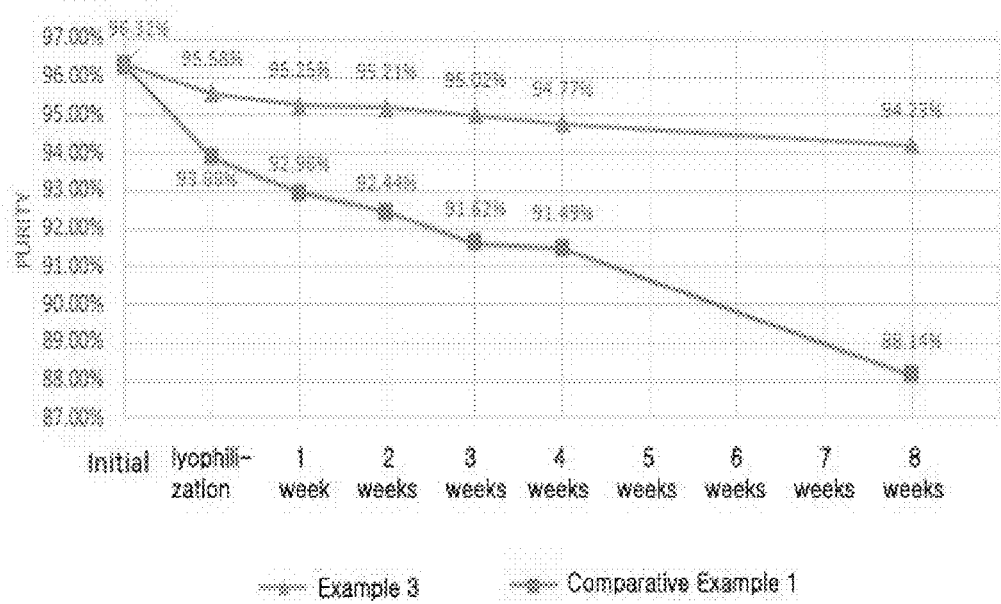
FIG. 2 shows the results obtained by measuring the purity changes of ertapenem in both the lyophilized formulation using NaHCO$_3$ as an additive and the lyophilized formulation prepared according to the present invention, at the preparations thereof; and then during the storages thereof at room temperature.
Figure 3:
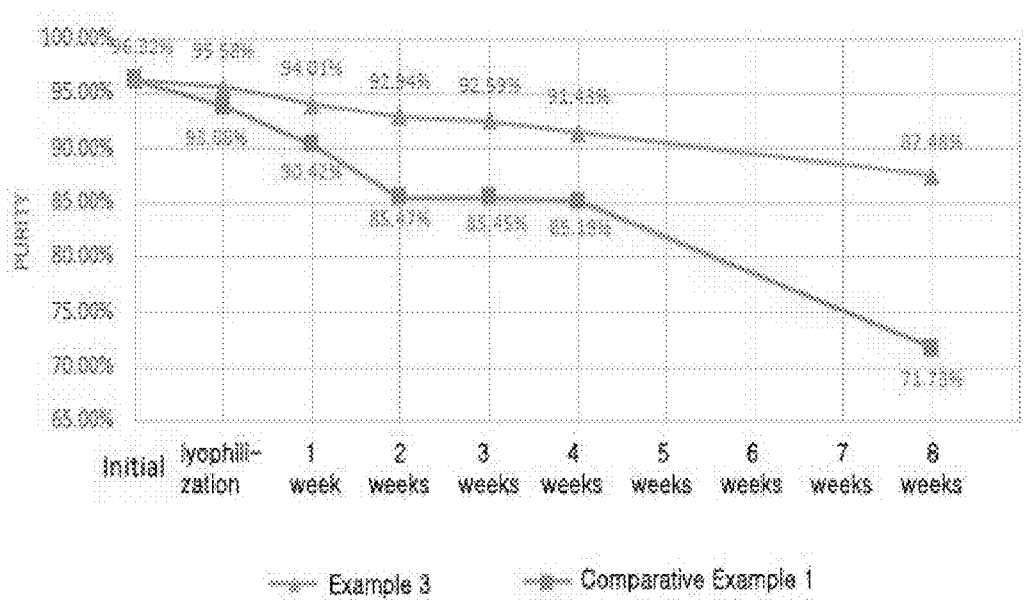
FIG. 3 shows the results obtained by measuring the purity changes of ertapenem in both the lyophilized formulation using NaHCO$_3$ as an additive and the lyophilized formulation prepared according to the present invention, at the preparations thereof; and then during the storages thereof under the accelerated (40° C., RH75%) condition.

As shown in Table 3 and FIGS. 1 to 3, the lyophilized formulation (Comparative Example 1) obtained from the solution containing the carbon dioxide source (NaHCO$_3$) showed remarkably decreased purity of ertapenem, i.e., from 96.32% to 93.88% (Δ 2.44%), while the lyophilized formulation (Example 3) obtained from the solution containing hydroxypropyl β-cyclodextrin showed only a slightly decreased purity of ertapenem, i.e., from 96.32% to 95.58% (Δ 0.74%). When the obtained lyophilized formulations were stored at low temperature (−20° C.) for 8 weeks, the purity of ertapenem in the lyophilized formulation of Comparative Example 1 was decreased to 92.36% [Δ 1.52% (93.88%-92.36%), while that in the obtained lyophilized formulation of Example 3 was decreased only to 95.04% [Δ 0.54% (95.58%-95.04%)]. And also, when the obtained lyophilized formulations were stored at room temperature and under the accelerated condition for 8 weeks, the purity decline of ertapenem in the lyophilized formulation of Comparative Example 1 is remarkably higher than that in lyophilized formulation of Example 3. Therefore, from the above results, it can be seen that hydroxypropyl β-cyclodextrin functions as a stabilizing agent as well as a cryoprotective agent.

Example 4: Preparation of Lyophilized Formulation of Other Carbapenem Antibiotics and Evaluation Thereof We evaluated whether or not hydroxypropyl β-cyclodextrin can also function both as a cryoprotective agent and as a stabilizing agent in the lyophilized formulations containing carbapenem antibiotics other than ertapenem. That is, the lyophilized formulations were prepared according to the same methods as in Example 3, using doripenem monohydrate and meropenem trihydrate instead of ertapenem monosodium salt.

TABLE 4

Lyophilized formulation containing doripenem monohydrate

| Additive | Storage condition | Before the lyophi-lization | Right after the lyophi-lization | Purity | | |
|---|---|---|---|---|---|---|
| | | | | 1 week | 2 weeks | 4 weeks |
| — | −20° C. | 99.64% | 97.99% | 98.10% | 97.80% | 96.47% |
| | Room temperature | | | 97.02% | 95.65% | 95.01% |
| | 40° C., 75% | | | 94.25% | 90.07% | 88.27% |
| HP-β-CD (1 eq.) | −20° C. | | 97.40% | 98.12% | 97.79% | 97.31% |
| | Room temperature | | | 97.61% | 96.16% | 94.55% |
| | 40° C., 75% | | | 94.24% | 87.76% | 85.83% |

TABLE 5

Lyophilized formulation containing meropenem trihydrate

| Additive | Storage condition | Before the lyophi-lization | Right after the lyophi-lization | Purity | | |
|---|---|---|---|---|---|---|
| | | | | 1 week | 2 weeks | 4 weeks |
| — | −20° C. | 97.94% | 95.75% | 94.95% | 94.68% | 94.60% |
| | Room temperature | | | 90.73% | 89.03% | 85.18% |
| | 40° C., 75% | | | 72.33% | 66.17% | 57.40% |
| HP-β-CD (1 eq.) | −20° C. | | 94.49% | 93.74% | 93.32% | 93.25% |
| | Room temperature | | | 84.15% | 81.57% | 73.00% |
| | 40° C., 75% | | | 44.59% | 44.17% | 32.36% |

As shown in Table 4 and Table 5, hydroxypropyl β-cyclodextrin did not function as a cryoprotective agent nor as a stabilizing agent, in the lyophilized formulations containing doripenem or meropenem.

The invention claimed is:
1. A process for preparing an ertapenem-containing lyophilized formulation, comprising (a) dissolving ertapenem or its pharmaceutically acceptable salt in a solu- tion of hydroxypropyl β-cyclodextrin, while maintaining the pH of the solution in the range of 6.5 to 8.0; and (b) lyophilizing the solution obtained in the step (a).

2. The process according to claim 1, wherein the hydroxypropyl β-cyclodextrin has a molar substitution ranging from 0.6 to 0.9.

3. The process according to claim 1, wherein the hydroxypropyl β-cyclodextrin is used in a ratio of 0.5 to 2.0 equivalents per 1 equivalent of ertapenem or its pharmaceutically acceptable salt.

4. The process according to claim 1, wherein the pharmaceutically acceptable salt of ertapenem is ertapenem monosodium salt.

5. The process according to claim 1, wherein the pH is adjusted with a base selected from the group consisting of sodium hydroxide, sodium bicarbonate, sodium carbonate, sodium methoxide, sodium ethoxide, and sodium t-butoxide.

* * * * *